United States Patent [19]
Harris

[11] Patent Number: 4,995,389
[45] Date of Patent: * Feb. 26, 1991

[54] MULTIELECTRODE QUICK CONNECT CARDIAC PACING LEAD CONNECTOR ASSEMBLY

[75] Inventor: Donald L. Harris, Key Largo, Fla.

[73] Assignee: Telectronics Pacing Systems, Inc., Suffield, Conn.

[*] Notice: The portion of the term of this patent subsequent to Dec. 29, 2004 has been disclaimed.

[21] Appl. No.: 809,665

[22] Filed: Dec. 16, 1985

[51] Int. Cl.⁵ ............................................. A61N 1/00
[52] U.S. Cl. ............................................. 128/419 P
[58] Field of Search ........ 128/419 P, 419 PG, 419 D, 128/783–786, 419 PS; 439/435–441, 761, 816, 860, 863

[56] References Cited

U.S. PATENT DOCUMENTS

| | | | |
|---|---|---|---|
| Re. 31,990 | 9/1985 | Sluetz et al. | 128/419 P |
| 3,676,829 | 7/1972 | Gartland, Jr. et al. | 439/816 X |
| 3,866,616 | 2/1975 | Purdy et al. | 128/419 PS |
| 4,013,081 | 3/1977 | Kolenk | 128/419 P |
| 4,112,953 | 9/1978 | Shanker et al. | 128/419 P |
| 4,142,532 | 3/1979 | Ware | 128/419 P |
| 4,180,078 | 12/1979 | Anderson | 128/419 PG |
| 4,182,345 | 1/1980 | Grose | 128/419 P |
| 4,226,244 | 10/1980 | Coury et al. | 128/419 P |
| 4,437,720 | 3/1984 | Harbaver | 439/435 |
| 4,445,511 | 5/1984 | Cowdery et al. | 128/419 P |
| 4,479,489 | 10/1984 | Tucci | 128/419 P |
| 4,583,543 | 4/1986 | Peers-Trevarton | 128/419 P |
| 4,712,557 | 12/1987 | Harris | 128/419 P |
| 4,715,380 | 12/1987 | Harris | 128/419 P |

*Primary Examiner*—Max Hindenburg
*Attorney, Agent, or Firm*—Thomas R. Vigil

[57] ABSTRACT

The cardiac pacing system includes a cardiac pacer and a multiconductor pacing lead having a distal end and a proximal end. The pacer comprises a metal case with insulated conductor feedthroughs in a top side thereof and a neck mounted to the top side of the metal case. The neck is made of a soft pliable material and spring contacts are provided in the neck for connecting the cardiac pacer with the pacing lead.

24 Claims, 3 Drawing Sheets

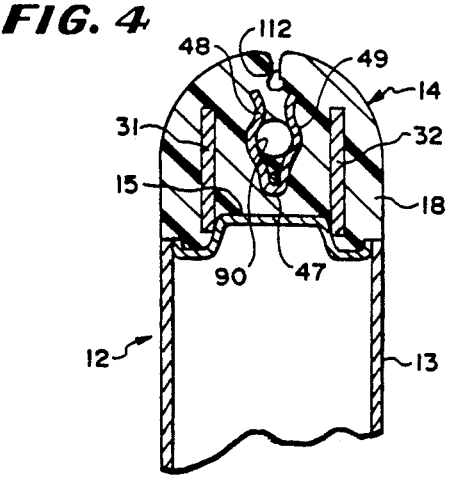
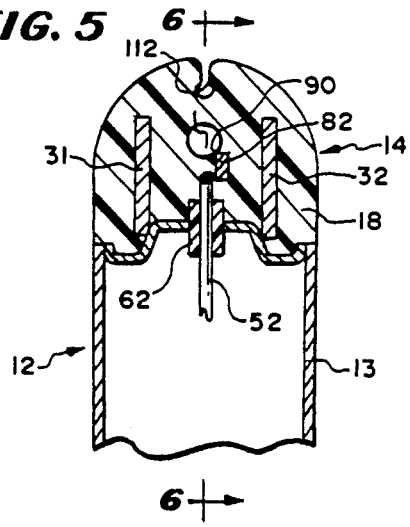
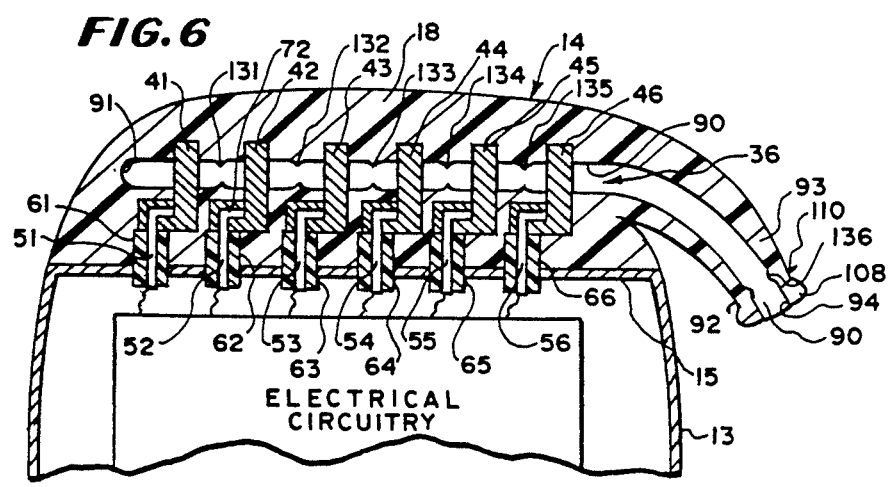
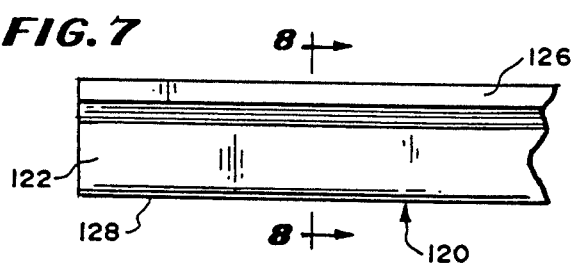
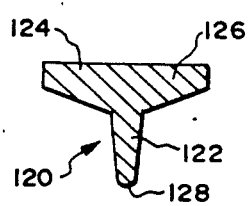

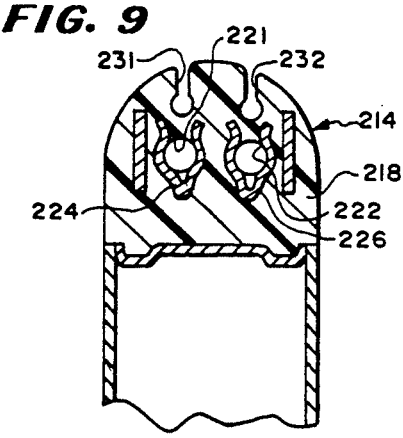
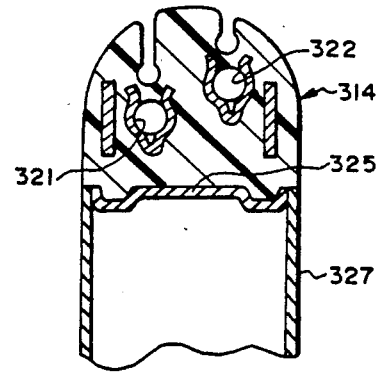
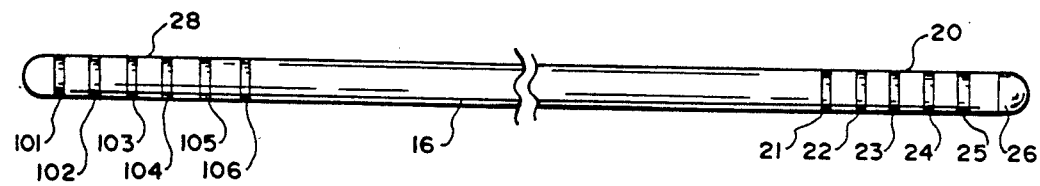

MULTIELECTRODE QUICK CONNECT CARDIAC PACING LEAD CONNECTOR ASSEMBLY

BACKGROUND OF THE INVENTION

1. Field of the Invention

The present invention relates to connector assemblies for cardiac pacing leads, and more particularly to a connector assembly which readily connects with an in-line multielectrode pacing lead. The connector assembly is designed to be expandable to accommodate a plurality of electrical contacts on the pacing lead and is mounted in a soft, pliable, so-called pacer neck, which fits closely about the pacing lead to prevent fluid flow into the connector assembly and between the electrical contacts.

2. Description of the Prior Art

Pacing systems include a pacer, which comprises a metal container or case which contains electronic circuitry and a power supply, and a pacing lead. The proximal end of the lead is connected to output terminals of the pacer in a component of the pacer which is commonly referred to as the neck of the pacer mounted to a top side of the case.

Multiple electrode cardiac pacing leads are well known and have been utilized for pacing both the atrial and ventricular chambers of the heart. Such a pacing lead includes a multipolar electrode assembly at the distal end and terminal connectors or contacts at the proximal end. The multipolar electrodes at the distal end of the lead usually consist in a tip electrode and one or more ring electrodes along the length of the lead. Additionally, the lead may contain one or more sensors along its length which measure and monitor physiological parameters such as the partial pressure of oxygen or carbon dioxide within the chambers of the heart.

In a pacing system with one electrode on the pacing lead, the distal end of the lead contains the electrode and is usually placed in the ventricle of the heart. The electrode is connected to the lead by an insulated helically coiled wire. At the proximal end of the lead, a terminal pin is affixed to the lead. This pin is inserted into the pacer neck where it makes contact with a pacer lead connector which is in turn connected to the cardiac pacer circuit and power source.

With one electrode on the distal end of the lead, referred to as a unipolar system, one pacer lead connector is needed in the neck of the pacer. In this instance, the case or can of the pacer, which is normally metal, serves as an anode. In a bipolar system, where two electrodes are on the distal end of the lead, two pacer lead connectors are necessary in the neck of the pacer.

Currently, cardiac pacing systems focus upon the sensing of electrical signals generated by the myocardium or middle layer of either the atrial and/or ventricular chambers of the heart and the stimulation of one or both of these chambers in the absence of spontaneous electrical activity. In such a system, either two different leads are used or the lead used measures ventricular activity at its tip and atrial activity along its length and therefore, more than one connector is needed in the pacer neck. Here, in a unipolar system, two pacer lead connectors are required in the neck of the pacer; one for the atrial lead terminal and one for the ventricular lead terminal. In a bipolar system, four pacer lead connectors are required in the pacer neck to monitor both chambers of the heart.

Future pacing systems will include physiological sensors as part of the pacing lead or separate from it. These physiological sensors will measure parameters such as oxygen and carbon dioxide levels, pH or any combination thereof, to name a few. These parameters will be transmitted to the pacer circuitry for use in setting various pacer outputs. Additionally, each of these sensors will require an electrical contact within the pacer neck in addition to the contacts mentioned above for sensing electrical activity.

The type of multielectrode pacing lead or leads most suitable for this type of multilead and sensor system is a lead with multiple electrodes in an in-line arrangement. These leads allow the monitoring of several different parameters while only causing one insertion to be made into the heart which reduces trauma. An example of such a lead is disclosed in U.S. Pat. No. 4,469,104 which discloses a lead assembly for a body implantable tissue stimulator which contains a connector in the pacer neck which relies on a garter spring or an elastomeric conductive O-ring to contact the in-line electrode terminals at the proximate end of the lead. Although such a lead is effective, the connector used is hard to manufacture, does not maintain good electrical contact, is difficult to insert into and is too large to accommodate a large number of electrode terminals within the minute confines of the pacer neck.

Heretofore various connectors have been utilized for connecting the proximal end of a single or multielectrode pacing lead to the electrical outputs in the neck of a pacer. The most common type of connector employs a terminal pin on the proximal end of the pacing lead which is secured inside the connector of the pacer by a set screw. This arrangement is not completely desirable since it usually requires the surgeon to tighten the screw after the terminal pin of the lead is in place inside the neck of the pacer during implantation in a body. Such a procedure is complicated due to the small size of the screw and the conditions of the operating room.

Additionally the number of contacts for a multielectrode lead is restricted if a different set screw is needed for each electrode contact within the connector. Present connectors which employ such a set screw connector are limited to a maximum of 4 connectors due to the size limitations of the pacer neck.

Finally, this set screw also encounters problems with body fluids over an extended period of time which causes deterioration of the screw and entry of fluid into the electrical contact area causing damage and malfunction. In some instances, a cap has been used to cover the screw head but such a design has not been entirely effective and has further complicated the installation procedure.

Therefore, the need exists for a multiple contact connector or assembly in a pacer neck which is small in size, easy to manufacture, readily accommodates a multielectrode lead, is impervious to body fluids and can be adapted to receive numerous electrode leads which vary upon the number needed for each particular patient.

As will be described in greater detail hereinafter, the assembly of the present invention provides a device which is capable of readily accommodating an in-line multielectrode lead without any additional complex installation procedures and is completely sealed from the body in which it is implanted.

Moreover, the connector assembly of the present invention differs from the previously proposed connector assemblies and pacer neck constructions by providing a connector assembly and pacer neck construction which is small in size, contains its own strain relief for the lead end portion received therein, is easy to use, can accommodate a large number of electrode contacts, which are easy to manufacture, and which maintain high reliability of electrical contact throughout the life of the pacing system.

SUMMARY OF THE INVENTION

According to the invention there is provided a cardiac pacing system including:

a multiconductor, multielectrode pacing lead having a distal end and a proximal end, and a cardiac pacer comprising a metal case with a plurality of insulated conductor feedthroughs in a top side thereof and a neck mounted to said top side of said metal case, said neck being made of a soft pliable material, flexible means within said neck material for connecting each insulated conductor feedthrough to a specific electrode of a multielectrode pacing lead, said flexible connecting means comprising a plurality of U-shaped electrical contacts, each having a bight and two upstanding legs for contacting ring contacts at the proximal end of the pacing lead, said neck having a lumen with a closed proximal end and an open distal end which receives said multiconductor pacing lead, said upstanding legs of each U-shaped electrical contact straddling the lumen in position of flexibly engage and grip a respective ring contact on the pacing lead, and said neck having a slit on its top side extending along the length of the neck and inwardly to a position above said lumen and between upper ends of said two upstanding legs of each U-shaped contact.

Further according to the invention there is provided a cardiac pacing system including a multiconductor, multielectrode pacing lead having a distal end and a proximal end and a cardiac pacer comprising a metal case with a plurality of insulated conductor feedthroughs in a top side thereof and a neck mounted to said top side of said metal case, said neck being made of a soft pliable material, flexible means within said neck material for connecting each insulated conductor feedthrough to a specific electrode of a multielectrode pacing lead, said flexible connecting means comprising a plurality of U-shaped electrical contacts, each having a bight and two upstanding legs for contacting ring contacts at the proximal end of the pacing lead, said neck having a lumen with a closed proximal and an open distal end which receives said multiconductor pacing lead, said upstanding legs of each U-shaped electrical contact straddling said lumen in position to flexibly engage a respective ring contact on the pacing lead, means in said neck for reinforcing said neck for reinforcing said neck along its length, and said reinforcing means comprising two parallel reinforcing bars each one of which extends from approximately said closed end to approximately said open end of said neck and to one side of said lumen.

Still further according to the invention there is provided a cardiac pacing system including a multiconductor, multielectrode pacing lead having a distal end and a proximal end and a cardiac pacer comprising a metal case with a plurality of insulated conductor feedthroughs in a top side thereof and a neck mounted to said top side of said metal case, said neck being made of a soft pliable material, flexible means within said neck material for connecting each insulated conductor feedthrough to a specific electrode of a multielectrode pacing lead, said flexible connecting means comprising a plurality of U-shaped electrical contacts each having a bight and two upstanding legs for contacting ring contacts on said proximal end of said pacing lead, said neck having a lumen with a closed proximal end and an open distal end which receives said multiconductor pacing lead, said upstanding legs of each U-shaped electrical contact straddling said lumen and flexibly engaging a respective ring contact on said pacing lead, and said neck having a plurality of radial projections protruding into said lumen of said neck for sealing said neck against said pacing lead at various points long said pacing lead between ring contacts thereof.

BRIEF DESCRIPTION OF THE DRAWINGS

FIG. 4 is a sectional view through one of the output terminal connectors or contacts of the pacer with the pliable neck in place and is taken along line 4—4 of FIG. 3.

FIG. 5 is a sectional view through the neck of the pacer, similar to the view shown in FIG. 4, and is taken along line 5—5 of FIG. 3.

FIG. 6 is a sectional view through the neck of the pacer and is taken along line 6—6 of FIG. 5.

FIG. 7 is a side view of an insertion tool which can be inserted into the neck shown in FIG. 6.

FIG. 8 is a sectional view of the insertion tool shown in FIG. 7 and is taken along line 8—8 of FIG. 7.

FIG. 9 is a vertical sectional view of another embodiment of the neck of the pacer, and shows two parallel rows of output terminal connectors or contacts whereby two pacing leads can be connected to the pacer.

FIG. 10 is a vertical sectional view of still another embodiment of the neck of the pacer, and shows staggered parallel rows of output terminal connectors or contacts.

FIG. 11 is a plan view of a multielectrode lead having a proximal terminal connector assembly adapted to be received in the neck of the pacers shown in FIGS. 4, 9 or 10.

DESCRIPTION OF THE PREFERRED EMBODIMENT(S)

Figure 1:
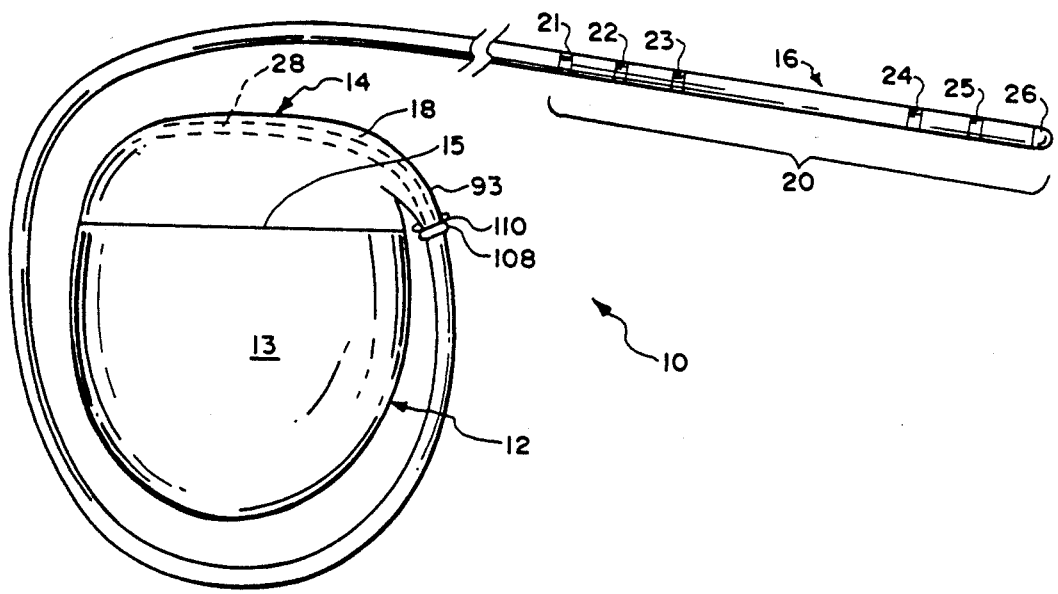
FIG. 1 is a side view of a cardiac pacing system including a multielectrode pacing lead and a pacer constructed according to the teachings of the present invention.

Referring now to the drawings in greater detail, there is illustrated in FIG. 1 a cardiac pacing system 10 including a pacer 12 comprising a metal case 13 and a neck 14 fixed to the top side 15 of the case 13 and a pacing lead 16 which is received in the neck 14 as will be described in greater detail hereinafter.

The pacer case 13 contains electronic/electrical circuitry and a power supply which are not part of the present invention and which are not shown in the figures.

In accordance with the teachings of the present invention and as will be described in greater detail hereinafter, the neck 14 includes a soft, pliable body 18 that is made of a soft pliable material such as an elastomeric material sold under the trademark Silastic ™. Preferably, the body 18 is molded onto the top side 15 of the pacer case 13.

As shown in FIG. 1, a distal end portion 20 of the pacing lead 16 has five ring electrodes 21-25 and a tip electrode 26. Then a proximal end 28 (hidden from view in FIG. 1) is received within the body 18, as will be described in greater detail hereinafter.

Figure 2:
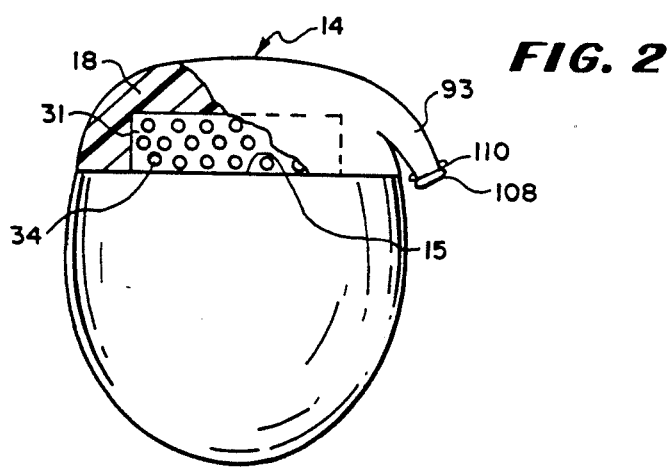
FIG. 2 is a side view of the pacer shown in FIG. 1 and shows a cut-a-way portion of a pliable neck of the pacer.

Referring now to FIGS. 2, 4 and 5, the pacer 12, to provide rigidity to the soft body 18 of the neck 14, includes two parallel spaced reinforcing bars 31 and 32 positioned in the body 18, as best shown in FIGS. 4 and 5. Preferably, each of the reinforcing bars 31 and 32 is made of titanium and has a plurality of holes 34 (FIG. 2) therein to facilitate gripping engagement of the soft, pliable elastomeric body 18 to and about the reinforcing bars 31 and 32 when the elastomeric body 18 of the neck 14 is molded onto the top side 15 of the pacer case 13. The reinforcing bars 31, 32 extend in the long direction of the neck 14 and can be welded to the top side 15 of the case 13.

Figure 3:
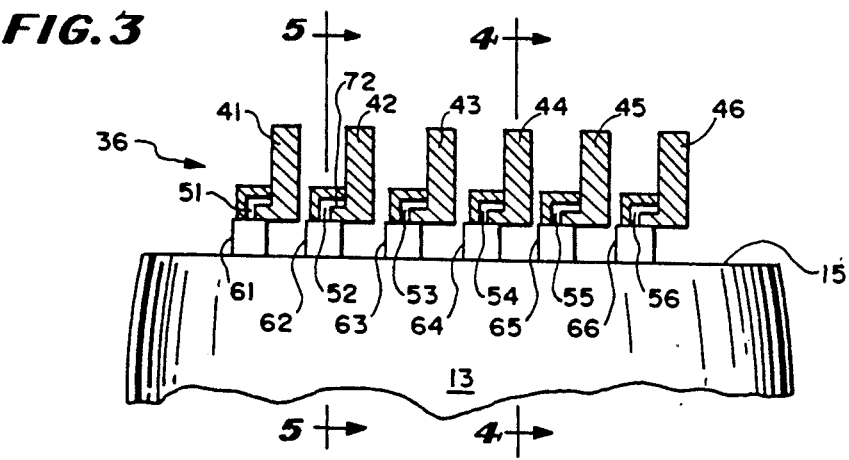
FIG. 3 is an enlarged fragmentary side view of a pacer case with the pliable neck removed and shows a plurality of pacer output terminal connectors.

As best shown in FIGS. 3, 4 and 6, the pacer 12 has a plurality 36 of U-shaped spring contacts 41-46, each of which has a bight portion 47 and upstanding legs 48 and 49 (FIG. 4).

As best shown in FIGS. 5 and 6, a plurality of wire conductors 51-56 extend through respective ones of insulated feedthroughs 61-66 which are mounted in a sealed manner in the top side 15 of the pacer case 13, as best shown in FIG. 6.

As best shown in FIGS. 5 and 6, each wire conductor 51-56 extends upwardly through an insulated feedthrough 61-66 and then is bent at a right angle, such as the bent end 72 of the conductor 52. Then this bent end 72 is welded to a tab 82 which extends from the bight 47 of each of the spring contacts 41-46.

As shown in FIG. 4, each pair of legs 48 and 49 of each spring contact 41-46 is adapted to extend upwardly in the body 18 and communicates with or extends into a lumen 90 which is formed in the body 18 of the neck 14.

As shown in FIG. 6, the lumen 90 extends generally parallel to the top side 15 of the case 13 and has a closed proximal end 91 and a curved end 92 which extends through a curved, generally tubular, end portion 93 of the body 18 to an opening 94.

It will be understood that the proximal end 28 (FIGS. 1 and 11) having ring connectors or electrodes 101-106 thereon is adapted to be inserted through the open end 94 of the lumen 90 and the curved portion 92 of the lumen 90 and into the straight portion thereof to the proximal end 91 with the ring connectors 101-106 making contact with the respective spring contacts 41-46. The depth of the lumen 90 and the location of the ring connectors 101-106 are such that when the proximal end 28 of the lead 16 "bottoms" against closed end 91 of the lumen 90, the connectors 101-106 are in registry with and in contact with the respective contacts 41-46.

The curved tubing portion 93 functions as a strain relief mechanism for the pacing lead 16 received therein and a free end 108 thereof is flared, as shown, so that a suture 110 can be placed around the flared end 108 for anchoring the lead 16 into position as well as for retarding fluid entry into the lumen 90.

To facilitate insertion or removal of the proximal end 28 of the lead 16 into the lumen 90 and into contact with the U-shaped electrical spring contacts 41-46 an elongate slit 112 extends longitudinally along the top of the body 18 and into the body 18 to a position above the lumen 90 as shown in FIGS. 4 and 5.

This slit 112 serves to receive an insertion tool 120 which is shown in FIGS. 7 and 8. Such insertion tool 120 is elongate and has a T-shaped cross-section including a leg 122 of the T and two side arms 124 and 126 of the T as best shown in FIG. 8. It will be appreciated that the leg 122 flares outwardly and upwardly from a bottom edge 128 so that the leg 122 can serve as a wedge when it is inserted into the slit 112 and forced downwardly to spread the spring contacts 41-46 apart during either insertion of the proximal end 28 or removal of the proximal end 28 of the pacing lead 16 into or from the lumen 90.

When the insertion tool 120 is removed from the slit 112, the upper ends of the spring contacts 41-46 will move toward each other to grasp the proximal end 28 of the pacing lead 16 and particularly the ring connectors 101-106 thereon, and also force portions of the body 18 on either side of the slit 112 toward each other to form a fluid tight seal.

To further enhance sealing between the respective spring contacts 41-46, annular ribs 131-135 are formed in the cylindrical wall defining lumen 90 within the body 18, as best shown in FIG. 6. These annular ribs 131-135 will grip the proximal end 28 of the pacing lead in the area between the ring connectors 101-106, respectively, so as to form a fluid tight seal between adjacent ring connectors 101-106. An additional annular rib 136 can be provided in the tubular body 93 to seal the entry into the curved end portion 92 of the lumen 90.

As shown in FIG. 9, a modified neck body 218 can be provided with two spaced apart lumens 221 and 222 therein, each adapted to receive a respective group of spring contacts 224, 226.

In this way, the pacer neck 214 is adapted to receive the proximal end of two pacing leads 16.

In this embodiment, a elongate slit 231 extends downwardly onto the neck body 218 above the lumen 221 and a similar elongate slit 232 extends downwardly into the neck body 218 above the lumen 222 and each slot 231, 232 is adapted to receive the insertion tool 120.

In still another embodiment of a pacer neck 314, shown in FIG. 10, the neck 314 is provided with lumens 321 and 322 which are staggered from each other such that the axis of the lumen 322 is above the axis of the lumen 321 relative to a top side 325 of a pacer case or can 327.

Also, of course, the contacts extending into one lumen can be staggered along the lumen from or relative to contacts extending into the other lumen so that the contacts in the respective lumen are not adjacent each other but "staggered".

As shown in FIG. 1, an advantage of the pacer system 10 comprising the pacer 12 described above and illustrated in the drawings is that with the curved tubular end portion 93 extending outwardly and downwardly from the neck body 18, the pacing lead 16 can extend downwardly and around the bottom of the pacer case 13 as shown in FIG. 1 for taking up slack in the pacing lead.

The soft neck pacer 12 of the present invention described above and illustrated in the drawings has a number of advantages, some of which have been described above and others of which are inherent in the invention. Some of these advantages can be enumerated as follows.

First of all, the soft neck 14 enables a plurality of up to 8, 6 being shown, spring contacts 41, etc. to be mounted in the neck. In fact with the double lumen embodiments shown in FIGS. 9 and 10, up to 16 contacts can be provided in the neck 214 or 314 of the pacer 12.

Additionally, the slit 112 can be easily sealed as shown in FIGS. 4 and 6 to prevent access of fluid to the lead proximal end receiving lumen 90.

Prevention of shorting between the contacts 41, etc. is minimized by the provision of the annular rings 131–136 and the flared end 108 of the curved tubular portion 93 enables further sealing of the lumen 90 by the tying of a suture 110 around the curved tubular portion 93.

From the foregoing description, it will also be understood that modifications can be made to the pacing system 10 of the present invention without departing from the teachings of the invention. Accordingly, the scope of the invention is only to be limited as necessitated by the accompanying claims.

I claim:

1. A cardiac pacing system including:
a multiconductor, multielectrode pacing lead having a distal end and a proximal end, and
a cardiac pacer comprising a metal case with a plurality of insulated conductor feedthroughs in a top side thereof and a neck mounted to said top side of said metal case, said neck being made of a soft pliable material, flexible means within said neck material for connecting each insulated conductor feedthrough to a specific electrode of a multielectrode pacing lead, said flexible connecting means comprising a plurality of U-shaped electrical contacts, each having a bight and two upstanding legs for contacting ring contacts at the proximal end of the pacing lead, said neck having a lumen with a closed proximal end and an open distal end which receives said multiconductor pacing lead, said upstanding legs of each U-shaped electrical contact straddling the lumen in position to flexibly engage and grip a respective ring contact on the pacing lead, and said neck having a slit on its top side extending along the length of the neck and inwardly to a position above said lumen and between upper ends of said two upstanding legs of each U-shaped contact.

2. The system of claim 1 wherein said neck has a skirt or is flared at the distal end of said lumen for retarding fluid entry into said lumen and for providing a point of anchorage for said neck.

3. The system of claim 1 wherein a distal end portion of said neck is elongate, receives the proximal end of said pacing lead therein and therethrough and serves to relieve possible strain on the lead by preventing sharp bends in the lead portion within said elongate end portion.

4. The system of claim 3 wherein said elongate end portion is a generally curved tubular end portion.

5. The system of claim 1 including means in said neck for reinforcing said neck along its length.

6. The system of claim 1 wherein said soft pliable neck is made of an elastomeric material.

7. The system of claim 1 wherein said legs of said electrical contacts are flexible spring contacts.

8. The system of claim 1 further including a T-in-cross-section elongate tool which is adapted to be inserted in said slit for spreading said legs of said contacts apart to facilitate insertion and removal of said proximal end of said pacing lead into said lumen and between the legs of said contacts.

9. The system of claim 1 wherein said plurality of electrical contacts is eight in number.

10. The system of claim 1 including a second plurality of contacts mounted to the top side of said case and said neck having a second lumen and a second slit above said second lumen with said second plurality of contacts extending into said second lumen.

11. The system of claim 10 wherein the axis of said second lumen is above the axis of said first lumen in said neck such that said lumens and contacts therein are staggered, the second being above the first.

12. The system of claim 10 wherein the contacts extending into one lumen are staggered along that lumen relative to the contacts extending into the other lumen so that the contacts in the respective lumens are not adjacent each other but are staggered.

13. A cardiac pacing system including a multiconductor, multielectrode pacing lead having a distal end and a proximal end, and
a cardiac pacer comprising a metal case with a plurality of insulated conductor feedthroughs in a top side thereof and a neck mounted to said top side of said metal case, said neck being made of a soft pliable material, flexible means within said neck material for connecting each insulated conductor feedthrough to a specific electrode of a multielectrode pacing lead, said flexible connecting means comprising a plurality of U-shaped electrical contacts, each having a bight and two upstanding legs for contacting ring contacted at the proximal end of the pacing lead, said neck having a lumen with a closed proximal end and an open distal end which receives said multiconductor pacing lead, said upstanding legs of each U-shaped electrical contact straddling said lumen in position to flexibly engage a respective ring contact on the pacing lead, means in said neck for reinforcing said neck for reinforcing said neck along its length, and said reinforcing means comprising two parallel reinforcing bars each one of which extends from approximately said closed end to approximately said open end of said neck and to one side of said lumen.

14. The system of claim 13 wherein said reinforcing bars have a plurality of holes therethrough which facilitate molding of said pliable neck material to said reinforcing bars.

15. The system of claim 14 wherein said reinforcing bars are made of titanium.

16. The system of claim 13 wherein said neck has a skirt or is flared at the distal end of said lumen for retarding fluid entry into said lumen and for providing a point of anchorage for said neck.

17. The system of claim 8 wherein a distal end portion of said neck is elongate, receives the proximal end of said pacing lead therein and therethrough and serves to relieve possible strain on the lead by preventing sharp bends in the lead portion within said elongate end portion.

18. The system of claim 13 wherein said soft pliable neck is made of an elastomeric material.

19. A cardiac pacing system including a multiconductor, multielectrode pacing lead having a distal end and a proximal end and a cardiac pacer comprising a metal case with a plurality of insulated conductor feedthroughs in a top side thereof and a neck mounted to said top side of said metal case, said neck being made of a soft pliable material, flexible means within said neck material for connecting each insulated conductor feedthrough to a specific electrode of a multielectrode pacing lead, said flexible connecting means comprising a plurality of U-shaped electrical contacts each having a bight and two upstanding legs for contacting ring contacts on said proximal end of said pacing lead, said neck having a lumen with a closed proximal end and an open distal end which receives said multiconductor pacing lead, said upstanding legs of each U-shaped electrical contact straddling said lumen and flexibly engaging a respective ring contact on said pacing lead, and said neck having a plurality of radial projections protruding into said lumen of said neck for sealing said neck against said pacing lead at various points along said pacing lead between ring contacts thereof.

20. The system of claim 19 wherein said neck has a skirt or is flared at the distal end of said lumen for retarding fluid entry into said lumen and for providing a point of anchorage for said neck.

21. The system of claim 19 wherein a distal end portion of said neck is elongate, receives the proximal end of said pacing lead therein and therethrough and serves to relieve possible strain on the lead by preventing sharp bends in the lead portion within said elongate end portion.

22. The system of claim 19 wherein said soft pliable neck is made of an elastomeric material.

23. The system of claim 19 wherein said legs of said electrical contacts are flexible spring contacts.

24. A method of connecting an implantable multielectrode cardiac pacing lead to the electronic circuitry in a cardiac pacer comprising the steps of:

mounting flexible U-shaped spring contacts to the top side of a metal case of the pacer having insulated conductor-carrying feedthroughs extending therethrough;

enclosing said spring contacts in a soft pliable neck which contains a lumen which legs of said spring contacts straddle;

providing a slit in said neck above the lumen;

inserting an insertion tool into the slit;

expanding said legs of said spring contacts with said insertion tool;

inserting a proximal end of a multielectrode pacing lead into said lumen and within said legs of said spring contacts so that each spring contact is grippingly engaged to a particular electrode on the multielectrode lead; and causing contraction of said legs of said spring contacts around respective electrodes of said pacing lead by removing said insertion tool.

* * * * *